United States Patent [19]

Hirschberg

[11] 4,263,511

[45] Apr. 21, 1981

[54] TURBIDITY METER

[75] Inventor: Joseph G. Hirschberg, Coral Gables, Fla.

[73] Assignee: University of Miami, Coral Gables, Fla.

[21] Appl. No.: 974,313

[22] Filed: Dec. 29, 1978

[51] Int. Cl.³ ............................................. G01N 21/26
[52] U.S. Cl. .................................... 250/343; 356/340
[58] Field of Search ......... 250/338, 341, 343, 222 PC; 356/339, 340

[56] References Cited

U.S. PATENT DOCUMENTS

| | | | |
|---|---|---|---|
| 3,234,846 | 2/1966 | Cropper et al. | 356/339 |
| 3,278,753 | 10/1966 | Pitts | 250/564 |
| 3,406,289 | 10/1968 | Schleusener | 250/222 PC |
| 3,854,045 | 12/1974 | Breuer et al. | 250/343 X |
| 4,118,625 | 10/1978 | Underwood | 250/343 |

*Primary Examiner*—Davis L. Willis
*Attorney, Agent, or Firm*—Meredith P. Sparks

[57] ABSTRACT

An in situ turbidity meter, for measuring water quality of a body of water comprising a pulsed infrared laser which illuminates the water, thereby producing scattered radiation from particles suspended in the water. A portion of the scattered radiation is collected and correlated to the turbidity of the water.

7 Claims, 1 Drawing Figure

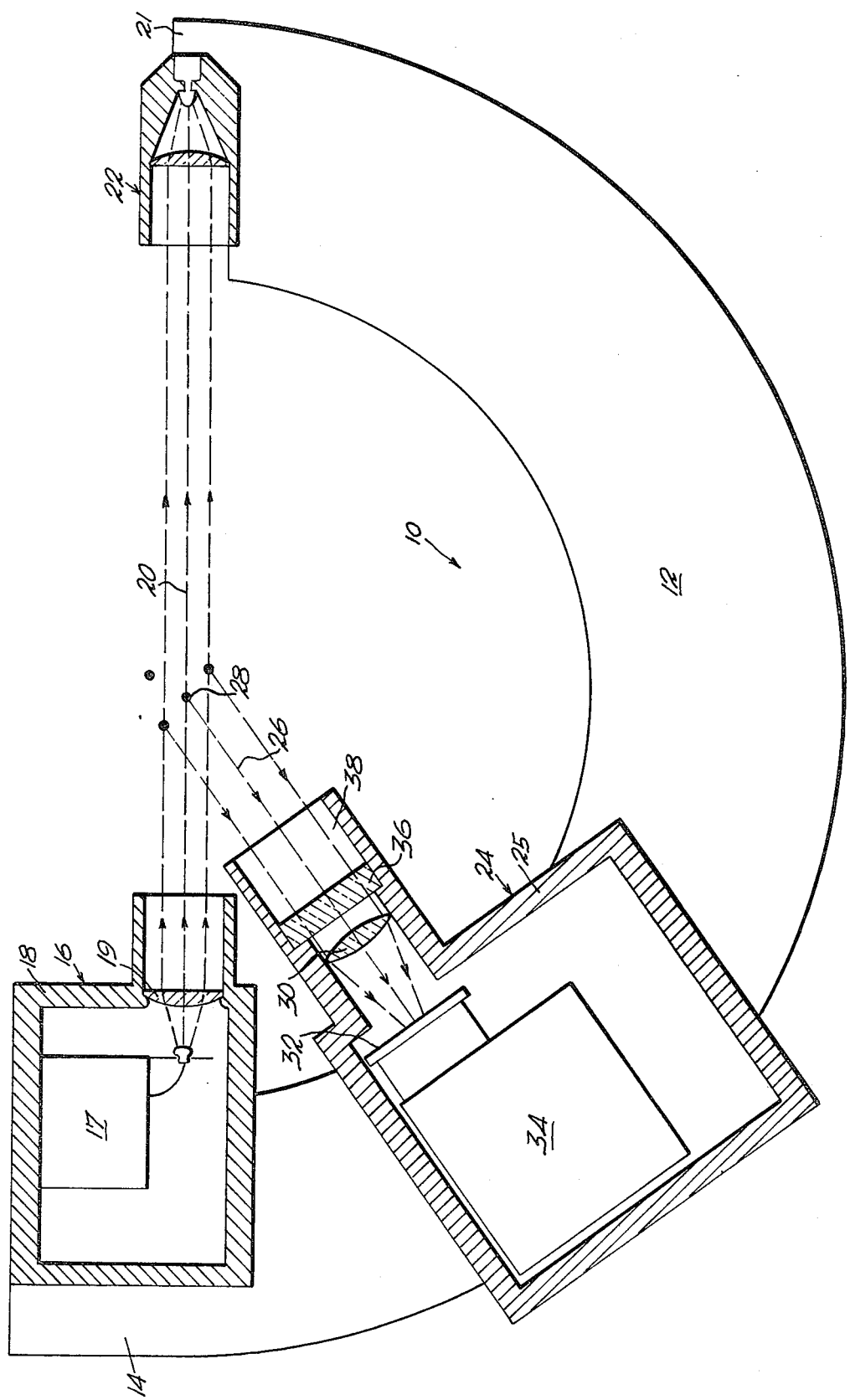

TURBIDITY METER

BACKGROUND OF THE INVENTION

1. FIELD OF THE INVENTION

The present invention relates to turbidity meters which measure the clarity of water in an oceanic or like environment.

2. DESCRIPTION OF THE PRIOR ART

Many of the recent studies of water quality, for example in various salt water bays, have emphasized the importance of water clarity among the indices describing the condition of the water. Turbidity of the water is a term generally applied to the clarity of the water, and, more specifically, to the cloudy or hazy appearance in a naturally clear liquid caused by a suspension of, for example, fine particles. However, in these studies almost all descriptions of water turbidity in such bodies of water are approximate and anecdotal in nature. Detailed qualitative information on turbidity seems to be lacking in most other studies of water quality in the coastal environment, as well.

One reason for this lack of information on what is certainly an important parameter in determining water quality, is the lack of a turbidity meter in the prior art which can be left in the body of water being monitored for a substantial period of time to record the information. Secondly, turbidity meter designs of the prior art have used complex systems of baffles or shutters to eliminate the effects of daylight interference. More specifically, the irradiating beams of the prior art devices normally comprise electromagnetic radiation having a wavelength in visible light spectrum. Hence, daylight interferes with scatter light detection, such detection being commonly used in these prior art turbidity meters. Therefore, a practical, functional turbidity meter does not exist in the prior art.

A practical, functional turbidity meter placed in strategic positions in an estuarine environment can provide invaluable data on the behavior of turbidity under various wind and tide conditions. In this way, a systematic approach to the question of water clarity in an environment, such as a bay, may be undertaken. Such a meter is also very attractive for use in monitoring operations such as dredging or filling, in order to make certain that environmental requirements are not being exceeded. However, the prior art has not provided a turbidity meter capable of achieving these objectives.

There are many discussions of turbidity in the literature, including both the effects of absorption and the scattering mainly due to particles suspended in the water. As has been pointed out, however, the principal problem in seeing through seawater is usually scattering by particles. The total scattering coefficient in the sea includes the effect of the water itself, dissolved material, and suspended particles. In any but the clearest water, however, the main contribution to the scattering coefficient is due to the suspended particles. If a volume V of water is irradiated by a beam of light of wavelength $\lambda$, then the intensity, I, of the light scattered into direction $\theta$ measured from the direction of the beam is given by $$I = \int_V \beta(\theta,\lambda) E\, dv,$$

where $\beta(\theta, \lambda)$ is the scattering function, which depends on both wavelength and scattering angle, and E is the incident irradiance into the volume element dv. This means that to obtain an exact determination of $\beta$, measurements must be made at all angles and all wavelengths. However, by comparing a portion of the scattering at a given angle to the total scattered light in all directions, it has been shown that for typical oceanic waters, measurements made at, for example 45°, will yield accurate values of the total scatterance within a few percent. This greatly simplifies the practical problem of measuring turbidity. In addition, it has been shown that the wavelength dependence of scattering from particles in the sea (most of which are larger than a micron in diameter) is very small.

The prior art may be illustrated by U.S. Pat. No. 3,278,753, to Pitts, showing an underwater detection system wherein light backscatter is utilized to detect the presence of an object. U.S. Pat. No. 3,406,289, to Schleusener, illustrates the use of an infrared laser in a cavity containing a gaseous medium.

SUMMARY OF THE INVENTION

The present invention relates to a submersible turbidity meter, for operation in a body of water, to measure and record water quality. The turbidity meter comprises a pulsed infrared laser which irradiates the water, thereby producing scattered infrared radiation from the particles. Some of the scattered radiation is collected and then correlated with known parameters to give detailed qualitative information of the turbidity of the water.

It was recognized that infrared radiation could be used in a turbidity meter without appreciably affecting the measured turbidity values. It is transmitted, however, only a short distance through the water, the length depending on wavelength. Hence, daylight interference, commonly affecting the prior art devices, is virtually eliminated in the present invention.

The monitoring of changing conditions in an oceanic environment requires a turbidity meter capable of monitoring operations over a substantial time period. Hence, utilization of a pulsed laser in the present invention provides high output power and a very efficient usage of that power to permit a continuous operation over a substantial period of time. These efficient, prolonged monitoring capabilities were not available in the prior art devices. The pulsed nature of the laser light enhances the performance of the unit in daylight.

The laser's small size, its efficiency, and the elimination of parasitic light interference, all combine to make a practical in situ recording meter available for the first time for studies of water quality.

BRIEF DESCRIPTION OF THE DRAWINGS

Further objects and advantages of the present invention will become apparent as the following description proceeds, taken in conjunction with the accompanying drawings in which:

The drawing shows the preferred embodiment of the turbidity meter of the present invention, with a cross section through the various housings.

DETAILED DESCRIPTION OF THE PREFERRED EMBODIMENT

Referring to the drawing, there is disclosed a turbidity meter, generally indicated as 10, for the measurement of water clarity in an oceanic or like water environment, such as a coastal environment. The turbidity meter 10 is adapted for efficient operation under the surface of the body of water for extended lengths of time. The turbidity meter 10 comprises a frame 12, having a preferably semicircular configuration, for mounting the components of the meter 10. Mounted at one end portion 14 of the frame 12 is a conventional infrared laser 16 in the form of a coherent light source of electromagnetic radiation in the infrared wavelength range. Moreover, the infrared laser is of a pulsed type, wherein a conventional pulser 17 produces a pulse of infrared radiation at fixed time intervals. In the illustrated embodiment, the laser 16 includes a housing 18, shown in cross section, and a convex, converging lens 19 for providing a collimated beam 20 of infrared radiation. It should be understood that the specific construction of the infrared laser is well known and may take different conventional forms. The infrared laser arrangement of the preferred embodiment is commercially available as a standard unit from Laser Diode Laboratories, Inc. of Metuchen, N.J.

Oppositely mounted from the laser 16 on end portion 21 is a conventional direct beam detector 22, preferably in the form of a photodiode tube. The detector 22 is configured and aligned to receive the collimated infrared radiation from the infrared laser 16. A second optical detector, a conventional scattered radiation detector 24, is adjustably secured to the frame 12 in a housing 25. The detector 24 is movable along the frame 12, and regardless of its location, the detector 24 is disposed with its center axis 26 positioned in intersecting relationship with a radius center 28 of the frame 12. Although this adjustable relationship of the detector 24 is desirable, it is not required for the invention. The specific construction of the scattered radiation detector, such as detector 24, for infrared radiation is well known. In the preferred embodiment, the scattered radiation detector 24 is commercially available as a standard unit from EG & G Inc. of Salem, Massachusetts. This conventional detector unit uses a convex lens 30 for concentrating the radiation on a photosensitive surface 32, which in turn converts radiation signals to electrical signals for detector electronics 34. Normally, a color discriminating filter 36 is interposed between the photosensitive surface 32 and the incoming optical signal. Typically, the detector 24 includes a conventional pulse height averaging circuit and buffer. Other infrared detector arrangements would also be usable in the present invention.

In operation, the turbidity unit 10 is immersed in water, for example, of a large body of water of a coastal environment. As previously explained, in such water there is normally a suspension of particles. In that the radiation impinges upon the particles, some radiation, designated as scattered radiation, is produced primarily by reflection from the particles, with some scattered radiation being produced by diffraction and refraction, mostly in a forward direction. Hence, that radiation which deviates in direction is scattered radiation. As previously explained, the principal problem in seeing through seawater is scattering by particles. Moreover, as previously explained, a given detected value of scattered radiation collected by one or more detectors 24 and collected in the direction of a given angle with respect to the collimated beam 20, can be correlated, in a known manner, with the amount of total scattered radiation. In the preferred embodiment, the scattered radiation detector 24 is aligned at approximately a 45° angle in a back scatter direction with respect to the collimated beam 20. Although this angle is desirable, in most situations in the ocean, any angle that receives scattered radiation that deviates from the incident beam is acceptable. Moreover, more than one detector 24 may be used. The direct beam detector 22 receives that portion of the incident collimated beam 20 which is not deflected or absorbed by the water itself, dissolved material, and suspended particles. With the two values of detected radiation from detectors 22 and 24, a determination of turbidity may be achieved using known calculation methods.

As previously explained, the wavelength dependence of scattering from particles in the sea is very small. The inventor concluded that measurements made from various parts of the electromagnetic spectrum, including the near infrared, do not appreciably affect the results. In providing the turbidity meter 10 for measuring scattering, the two principal problems of daylight interference, and the necessity for providing a very efficient radiation source, were solved. The small (thumbnail sized) infrared laser 16 has 20 to 30 watts peak power and very short (100-200 nanosecond) pulses. Such lasers have a double advantage in that they are very efficient, and they provide a means of eliminating the effects of daylight. Because of the short duty cycle of the laser 16 the detectors 22 and 24 only have to be receiving for very short periods during the laser pulses. The result is that the effect of daylight interference is reduced by a factor of $10^4$. In addition, the infrared wavelengths that are used (0.9 micrometer) have an absorption length in water, as measured in a laboratory, of 0.25 meter. This means that at a depth of 1 meter, the effects of daylight are further reduced by an additional factor of 55, and at a depth of 2 meters by almost 3,000. Thus the turbidity apparatus 10 can operate a meter or more beneath the surface with complete shielding from the effects of daylight. No complex system of baffles or shutters is necessary to eliminate parasitic light, such as is often used in other prior art instruments. These often cause difficulties since they tend to restrict the free flow of water, and in a tethered instrument would probably lead to incorrect results.

The other advantage of the infrared laser 16 is the direct result of a short duty cycle. The 100 nanosecond pulses are repeated every millisecond. This results in a duty cycle of $10^{-4}$. That means that even with a 20 watt peak pulse, only 2 milliwatts average power are actually used. Further, the laser 16 when collimated with a lens, concentrates practically all of its light into a beam which can be utilized. An incandescent lamp radiates in all directions and cannot be used with short pulser, so that the laser instrument will have a total efficiency advantage of about $10^5$ ($10^4$ from the duty cycle and $10^1$ from the beam concentration). The laser's small size, its efficiency, and the elimination of parasitic light interference all combine to make a practical in situ recording turbidity meter 10. This meter may be applied to the problem of determining the tidal, aeolian, seasonal, and secular changes of turbidity in a body of water, which can be any kind of water anywhere, for example, in the Artic Ocean. It should also be appreciated that the very small window 38 of the laser 16 avoids some of the problems of providing clear windows.

Typical values for a sample test using the turbidity meter 10 would be a $\beta(\theta)$ for very clear water of $2 \times 10^{-3} m^{-1} str^{-1}$, a collecting solid angle for the scattered radiation detector 24 of $3.7 \times 10^{-2}$, a scattering length of at least 1.2 cm (90°), laser power of 30 watts. This would lead to radiation being detected so as to create a pulse of 0.26 volts at an output of a detector whose noise is 2.5 mV. These are merely illustrative values.

Although particular embodiments of the invention have been shown and described here, there is no intention to thereby limit the invention to the details of such embodiments. On the contrary, the intention is to cover all modifications, alternatives, embodiments, usages and equivalents of the subject invention as fall within the spirit and scope of the invention, specification and the appended claims.

What is claimed is:

1. A submersible turbidity meter for continuously monitoring the quality of a large body of water over a substantial length of time comprising an open frame for mounting the components of said meter, said frame allowing the free flow of water therethrough;

a pulsed infrared laser means mounted on said frame for providing a pulsed collimated beam of infrared radiation;

a direct beam detector means oppositely mounted on said frame which is configured and aligned to receive said collimated beam of infrared radiation from said laser, and at least one scattered beam detector means secured to said frame which is movably adjusted on said frame so as to receive scattered radiation at any desired angle to said beam;

whereby the amount of infrared radiation scattered by particles present in said body of water can be monitored and recorded without daylight interference and with an infrared laser means which is an efficient energy source over a period of time during which the water can be subject to varying conditions.

2. The meter of claim 1 wherein said frame has a semicircular configuration.

3. The meter of claim 2 wherein said scattered beam detector means is adjustably secured to said semicircular frame, and disposed with its center axis positioned in intersecting relationship with the center of said frame.

4. The meter of claim 1 wherein said direct beam detector means is a photodiode tube.

5. The meter of claim 1 wherein said scattered radiation detector means is aligned at an acute angle with respect to said collimated beam.

6. The infrared laser of claim 1 which uses 20-30 watts at peak power.

7. The infrared laser of claim 1 which includes a pulser that operates at 100 to 200 nanoseconds.

* * * * *